United States Patent [19]

Meyer et al.

[11] 4,406,906

[45] Sep. 27, 1983

[54] CEREBRAL THERAPEUTIC AGENT AND ITS USE

[75] Inventors: Horst Meyer; Friedrich Bossert; Stanislav Kazda; Friedrich Hoffmeister, all of Wuppertal; Wulf Vater, Leverkusen, all of Fed. Rep. of Germany

[73] Assignee: Bayer Aktiengesellschaft, Leverkusen, Fed. Rep. of Germany

[21] Appl. No.: 346,319

[22] Filed: Feb. 5, 1982

Related U.S. Application Data

[63] Continuation of Ser. No. 27,540, Apr. 5, 1979, abandoned.

[30] Foreign Application Priority Data

Apr. 11, 1978 [DE] Fed. Rep. of Germany ....... 2815578

[51] Int. Cl.³ .............................................. A61K 31/44
[52] U.S. Cl. .................................................. 424/263
[58] Field of Search ......................... 424/263; 546/322

[56] References Cited

U.S. PATENT DOCUMENTS 3,799,934  3/1974  Meyer et al. ........................ 424/263

OTHER PUBLICATIONS

Chem. Abst., vol. 78-1603G (1973).

*Primary Examiner*—Stanley J. Friedman
*Attorney, Agent, or Firm*—Sprung, Horn, Kramer & Woods

[57] ABSTRACT

The invention provides pharmaceutical compositions and medicaments, useful for the treatment of cerebral disorders, wherein the active compound is 1,4-dihydro-2,6-dimethyl-4-(3'-nitrophenyl)-pyridine-3-($\beta$-methoxyethyl ester)-5-(isopropyl ester). Also included in the invention are methods for the use of said compositions and medicaments.

4 Claims, No Drawings

CEREBRAL THERAPEUTIC AGENT AND ITS USE

This is a continuation of application Ser. No. 027,540 filed Apr. 5, 1979 now abandoned.

The present invention relates to the use as a cerebral therapeutic agent of 1,4-dihydro-2,6-dimethyl-4-(3′-nitrophenyl)-pyridine-3-(β-methoxyethyl ester)-5-(isopropyl ester).

It is already known that 1,4-dihydropyridine derivatives can be used as coronary agents and agents against high blood pressure (compare DT-OS (German Published No.) 2,117,571). The above-mentioned compound has already been described, in British Pat. No. 1,358,951, as a compound having a coronary action. It has also been disclosed that certain basic 1,4-dihydropyridine esters have a cerebral action (compare DT-OS (German Published No.) 2,302,866 and DT-OS (German Published No.) 2,407,115).

It has been found that the compound 1,4-dihydro-2,6-dimethyl-4-(3′-nitrophenyl)-pyridine-3-(β-methoxyethyl ester)-5-(isopropyl ester) (hereinafter called Bay e 9736) has a very advantageous action on cerebral circulatory disturbances.

According to the present invention there are provided pharmaceutical compositions containing, as an active ingredient, 1,4-dihydro-2,6-dimethyl-4-(3′-nitrophenyl)-pyridine-3-(β-methoxyethyl ester)-5-(isopropyl ester) in admixture with a solid or liquefied gaseous diluent or in admixture with a liquid diluent other than a solvent of a molecular weight less than 200 except in the presence of a surface-active agent.

Surprisingly, the compound used according to the invention exhibits, in very low doses, a cerebral-specific action, which makes it possible to use it for the treatment of cerebral insufficiencies, in particular cerebral circulatory disturbances of various origins. The compound is superior to known substances having a cerebral action, both in the strength of its action and in its type of action and specificity.

It is particularly suitable for the treatment of cerebral vascular diseases due to age and sclerosis, as well as cerebral hypoxidoses, post-traumatic brain damage, general weaknesses in cerebral performance of vascular and metabolic origin, inbalance and other vestibular illnesses and defective vision of vascular origin.

Such a powerful and organ-specific cerebral action has not hitherto been disclosed with regard to the series of cerebral therapeutic agents known from the state of the art.

The compound 1,4-dihydro-2,6-dimethyl-4-(3′-nitrophenyl)-pyridine-3-(β-methoxyethyl ester)-5-isopropyl ester) is obtained in a manner which is in itself known, for example by reacting 3-nitrobenzylideneacetoacetic acid β-methoxyethyl ester with β-aminocrotonic acid isopropyl ester in an inert organic solvent at elevated temperature. The compound has a melting point of 125° C.

Further possible preparation processes are described in DT-OS (German Published No.) 2,117,571 and DT-OS (German Published No.) 2,117,573.

The advantageous organ-specific action of the compound according to the invention is coupled with a very good tolerance and a long-term period of action. A comparison with 2,6-dimethyl-4-(3′-nitrophenyl)-1,4-dihydropyridine-3,5-dicarboxylic acid 3-β-(N-benzyl-N-methylamino)ethyl 5-methyl ester, which is identified as a particularly active compound in DT-OS (German Published No.) 2,407,115, shows itself that the compound according to the invention causes not only a significantly greater increased cerebral blood supply, but, in addition to the longer period of action, also has a more advantageous action profile.

The surprising advantageous properties may be illustrated by the following investigations:

After enteral and parenteral administration in a wide range of doses to warm-blooded animals, such as dogs, cats, rats, rabbits, Rhesus monkeys and Saimiris monkeys, the compound according to the invention increases cerebral circulation. The cerebral-vaso dilating action is in the foreground of the action spectrum of the substance; it takes effect, after a low dosage and very specifically, in the cerebral vessels. This surprising predilectivity of the cerebro-vascular action significantly differentiates the compound according to the invention from all the commercially available preparations of this category, and from other dihydropyridine derivatives for which a certain cerebral-dilating action has been declared in animal experiments (compare DT-OS (German Published No.) 2,407,115; YC-93).

Effective prophylaxis and therapy of the consequences of an ischaemic cerebral insult can be carried out successfully with the compound according to the invention. Thus, for example, in cats, post-ischaemic restricted cerebral circulation is completely prevented, post-ischaemic changes in the electroencephalogram are significantly improved and the mortality after an experimental cerebral insult is drastically reduced.

The compound according to the invention is unrivalled in this cerebral anti-ischaemic action when administered to warm-blooded animals. It has not been possible to achieve such an action with any of the existing pharmaceuticals in this category.

Learning and memory disorders of vascular and non-vascular origin induced experimentally in rats and mice (cerebral ischaemia, hypoxia, convulsions and enforced lack of sleep, inter alia) are, surprisingly, significantly improved or completely restored to normal by treatment with the compound according to the invention. The compound is far superior to commercially available preparations in the extent of this action.

The surprising advantageous action of the compound according to the invention may be illustrated by way of example by the data in the following table.

TABLE

Action of substances on the circulation of the cerebral and extracerebral vessels in dogs

| Substance | Dose mg/kg, intravenously | Number of animals | Increase in the cerebral circulation ($^{133}$Xenon clearance) | Increase in circulation (electromagnetic flowmeter) | |
|---|---|---|---|---|---|
| | | | | A. carotis ext. | A. femoralis |
| BAY e 9736 | 0.01 | 22 | 30% | 26% | 0.5% |
| YC 93 | 0.01 | 3 | 16% | 40% | 10.0% |
| Bencyclane | 10.0 | 5 | 34% | — | 152% |

TABLE-continued

Action of substances on the circulation of the cerebral and extracerebral vessels in dogs

| Substance | Dose mg/kg, intravenously | Number of animals | Increase in the cerebral circulation ($^{133}$Xenon clearance) | Increase in circulation (electromagnetic flowmeter) | |
|---|---|---|---|---|---|
| | | | | A. carotis ext. | A. femoralis |
| ("Fludilat" (Trade Mark)) Cinnarizine ("Stutgeron" (Trade Mark)) | 10.0 | 4 | 43% | — | 65% |

The present invention also provides pharmaceutical compositions containing, as active ingredient, the compound of the invention in the form of a sterile and/or physiologically isotonic aqueous solution.

The invention also provides a medicament in dosage unit form comprising the compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third of a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 90% of the active ingredient by weight of the total composition.

In addition to the compound of the invention, the pharmaceutical compositions and medicaments according to the invention can also contain other pharmaceutically active compounds.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention to warm-blooded animals is 0.05 to 5 mg of active ingredient, and 0.5 to 25 mg of active ingredient for enteral administration.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the inention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally. Preferred pharmaceutical compositions and medicaments are therefore those adapted for administration such as oral administration. Administration in the method of the invention is preferably oral administration.

In general it has proved advantageous to administer amounts of from 0.0001 mg to 0.5 mg/kg, preferably 0.001 to 0.1 mg/kg, of body weight per day in the case of intravenous administration and 0.001 to 1 mg/kg, preferably 0.01 to 0.5 mg/kg, of body weight per day in the case of enteral administration, to achieve effective results. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the program of the disease or interval at which it is to be administered. Thus it may in some case sufficient to use less than the above mentioned minimum dosage rate, while in other cases the upper limit mentioned must be exceeded to achieve the desired results. Where larger amounts are administered it can be advisable to divide these into several individual administrations over the course of the day.

The following Examples illustrate pharmaceutical formulations according to the present invention.

EXAMPLE 1

Soft gelatine capsules with 5 mg of active compound per capsule.

A solution of the following composition is prepared for about 10,000 capsules:

| BAY e 9736, active compound | 58.8 g |
|---|---|
| Glycerol | 240.0 g |
| Polyethylene glycol 400 | 3,833.2 g |
| Water | 400.0 g |
| | 4,532.0 g |

The solution is filled into oblong soft gelatine capsules of size 6 minims. The capsules are suitable for chewing or swallowing.

EXAMPLE 2

Tablets, coated tablets or dragees with 10 mg of active compound:

The following amounts relate to the production of 100,000 tablets or cores:

| BAY e 9737, finely ground active compound | 1000 kg |
|---|---|
| Lactose | 10.25 kg |
| Starch | 2.70 kg |
| Microcrystalline cellulose | 2.70 kg |

The above constituents are mixed in a planetary mixer and are then mixed with a solution prepared from

| Polyvinylpyrrolidone (molecular weight, for example, 25,000) | 1.20 kg |
|---|---|
| Polysorbate 80 USP (Tween 80$^R$) and | 0.06 kg |
| Water   about | 4.00 kg | and the mixture is granulated in a manner which is in itself known, by grating the drying the moist mass.

| Magnesium stearate | 0.09 kg |
|---|---| is then added. The finished tablet mixture of 18 kg is pressed to convex tablets weighing 180 mg. The diameter of the tablets is 8 mm.

The tablets can be lacquered or coated in a manner which is in itself known.

EXAMPLE 3

Drops with 4 mg of active compound per ml: The following solution is prepared

| | For drops with 4 mg per ml |
|---|---|
| BAY e 9736, active compound | 4.0 g |
| 96% strength ethanol | 450.0 g |
| Liquid flavouring | 6.0 g |
| Methyl paraben | 1.0 g |
| Polyethylene glycol 400 | 50.0 g |
| 50% strength sugar syrup | 400.0 g |
| Foodstuff colorant (Gelborange S) | 0.6 g |
| Water to | 1,000.0 ml |

The active compound, methyl paraben and flavouring are dissolved at room temperature. Polyethylene glycol 400 and the 50% strength sugar syrup and then slowly added, whilst stirring, the colorant is dissolved and the solution is made up to 1,000 ml with water.

The solution is filled into brown bottles, it also being possible to add sweeteners, if desired.

EXAMPLE 4

| Syrup with 10 mg of active compound per 10 ml | |
|---|---|
| BAY e 9736, active compound | 1.0 g |
| Methyl paraben | 1.0 g |
| 96% strength ethanol | 250.0 g |
| Liquid flavouring | 4.0 g |
| Polyethylene glycol 400 | 100.0 g |
| Glycerol | 250.0 g |
| 50% strength sugar syrup | 300.0 g |
| Foodstuff colorant Gelborange S | 0.5 g |

| -continued | |
|---|---|
| Syrup with 10 mg of active compound per 10 ml | |
| Water to | 1,000.0 ml |

The preparation is carried out analogously to Example 3.

What is claimed is:

1. A method of combating pathologically reduced cerebral functions and performance weaknesses, cerebral insufficiency and disorders in cerebral circulation and metabolism in warm-blooded animals which comprises administering to the said animals a cerebral specific effective amount for treating said conditions of 1,4dihydro-2,6dimethyl-4-(3'-nitrophenyl)-pyridino-3-($\beta$-methoxyethyl ester)-5-isopropyl ester either alone or in admixture with a diluent or in the form of a medicament.

2. A method according to claim 1 in which the active compound is administered intravenously in an amount of 0.0001 to 0.5 mg per kg body weight per day, or enterally in an amount of 0.001 to 1 mg per kg body weight per day.

3. A method according to claim 1, in which the compound is administered intravenously in an amount of 0.001 to 0.1 mg per kg body weight per day, or enterally in an amount of 0.01 to 0.5 mg per kg body weight per day.

4. A method according to claim 1 or 2 in which the active compound is administered orally.

* * * * *

UNITED STATES PATENT AND TRADEMARK OFFICE

CERTIFICATE EXTENDING PATENT TERM
UNDER 35 U.S.C. 156

Patent No.      : 4,406,906

Dated           : September 27, 1983

Inventor(s)     : HORST MEYER ET AL

Patent Owner    : BAYER AKTIENGESELLSCHAFT

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156(b).

I have caused the seal of the Patent and Trademark Office to be affixed this 11th day of December 1989.

Jeffrey M. Samuels
Acting Commissioner of
   Patents and Trademarks